(12) United States Patent
Suppiger et al.

(10) Patent No.: US 10,695,461 B2
(45) Date of Patent: Jun. 30, 2020

(54) DRIED IMPLANT COMPOSITION AND INJECTABLE AQUEOUS IMPLANT FORMULATION

(71) Applicant: GEISTLICH PHARMA AG, Wolhusen (CH)

(72) Inventors: Daniel Suppiger, Rotkreuz (CH); Paul Buxton, Lucerne (CH); Nino Kurz, Langnau im Emmental (CH)

(73) Assignee: Geistlich Pharma AG, Wolhusen (CH)

( * ) Notice: Subject to any disclaimer, the term of this patent is extended or adjusted under 35 U.S.C. 154(b) by 0 days.

(21) Appl. No.: 16/220,306

(22) Filed: Dec. 14, 2018

(65) Prior Publication Data
US 2019/0209735 A1    Jul. 11, 2019

(30) Foreign Application Priority Data
Dec. 14, 2017  (EP) .................................... 17207341

(51) Int. Cl.
*A61L 27/24* (2006.01)
*A61L 27/46* (2006.01)
*A61L 27/50* (2006.01)
*A61L 24/00* (2006.01)

(52) U.S. Cl.
CPC ........... *A61L 27/24* (2013.01); *A61L 24/0015* (2013.01); *A61L 27/46* (2013.01); *A61L 27/50* (2013.01); *A61L 2400/06* (2013.01); *A61L 2430/02* (2013.01); *A61L 2430/12* (2013.01)

(58) Field of Classification Search
None
See application file for complete search history.

(56) References Cited

U.S. PATENT DOCUMENTS

| | | | |
|---|---|---|---|
| 5,167,961 A | 12/1992 | Heinz | |
| 5,352,715 A * | 10/1994 | Wallace | ................... A61L 27/10 523/115 |
| 7,322,825 B2 | 1/2008 | Szymaitis | |
| 2003/0026770 A1 * | 2/2003 | Szymaitis | ................ A61L 27/24 424/50 |
| 2007/0026030 A1 * | 2/2007 | Gill | ..................... A61B 17/7095 424/423 |
| 2012/0107401 A1 | 5/2012 | McKay | |
| 2016/0106674 A1 * | 4/2016 | Scalesciani | ......... A61L 26/0033 424/489 |

FOREIGN PATENT DOCUMENTS

| | | |
|---|---|---|
| EP | 0 270 254 A2 | 6/1988 |
| EP | 2 654 816 B1 | 2/2015 |

OTHER PUBLICATIONS

Sheikh et al., "Natural graft tissues and synthetic biomaterials for periodontal and alveolar bone reconstructive applications: a review," Biomaterials Research, published Jun. 5, 2017, p. 1-20.*
Geistlich Bio-Oss et al: "Proven Clinical Efficiency Key to Success of Nascent European Bone Graft Substitutes Market", PR Newswire, Sep. 6, 2004 (Sep. 6, 2004), XP55566242, Retrieved from the Internet: URL:https://www.geistlich-na.com/fileadmin/contenVGeistlich_USA/Documents/PDFs/Product_Brochures/GPNA-BoneSubstituteBrochure_2018.pdf, 16 pgs.
Daniele Cardaropoli et al: "Bio-Oss collagen and orthodontic movement for the treatment of infrabony defects in the esthetic zone", The International journal of periodontics & restorative dentistry, Dec. 1, 2006 (Dec. 1, 2006), p. 553, XP55566245, United States Retrieved from the Internet: URL:http://coimplante.odo.br/Biblioteca/J%20Peridontics%20Restorative%20DenVprd_26_6_Cardaropoli_4.pdf, 8 pgs.
Adileh Shirmohammadi et al., "Comparative Study on the Efficacy of Anorganic Bovine Bone (Bio-Oss) and Nanocrystalline Hydroxyapatite (Ostim) in Maxillary Sinus Floor Augmentation", International Scholarly Research Notices, vol. 2014, Jan. 1, 2014 (Jan. 1, 2014), pp. 1-7, XP55566246, DOI: 10.1155/2014/967091.
Notification of Transmittal of the International Search Report and the Written Opinion of the International Searching Authority, or the Declaration dated Mar. 19, 2019 cited in PCT/EP2018/085018, 18 pages.
Extended European Search Report cited in European Application No. 17207341.3, dated Jun. 6, 2018, 10 pages.

* cited by examiner

*Primary Examiner* — Monica A Shin
(74) *Attorney, Agent, or Firm* — Rothwell, Figg, Ernst & Manbeck, P.C.

(57) ABSTRACT

A dried implant composition for preparing an injectable aqueous implant formulation that is extrudable through a tapering system and a gauge 18 cannula, including a mixture of nanocrystalline hydroxyapatite particles derived from natural bone having a size of 50 to 200 μm and fragments of naturally crosslinked fibrous collagen material that pass through a 0.5 mm sieve; an injectable aqueous implant formulation for use in a method of oral tissue regeneration, wherein the injectable aqueous implant formulation is obtainable by hydration and homogeneous mixing; a process for preparing the injectable aqueous implant formulation; and a kit for preparing the injectable aqueous implant formulation for use in oral tissue regeneration.

20 Claims, 5 Drawing Sheets

Fig. 2

Bone-Cement Delivery System
Operating Instruction (using plunger)

MEDMIX

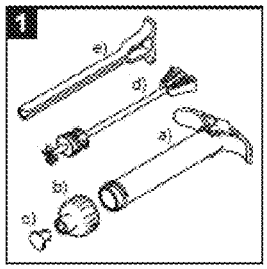

Step 1:
Identification of the system parts:
a) Syringe
b) Syringe cap
c) Luer-cap
d) Mixing device
e) Plunger

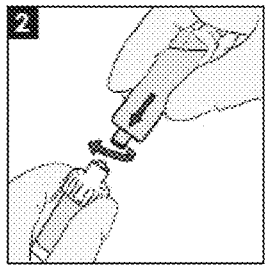

Step 2:
Remove the luer-cap from the syringe cap. Attach the container with liquid by turning the container clockwise onto the syringe cap.

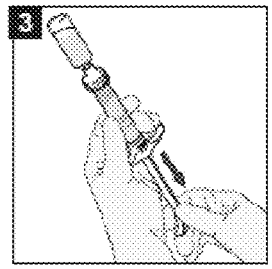

Step 3:
Aspirate the liquid from the container by pulling the plunger. Repeat if necessary.

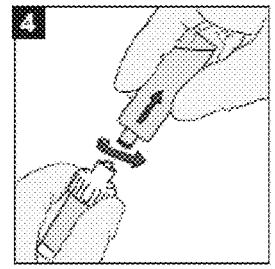

Step 4:
Remove the container by turning counter clock-wise while fixing the syringe cap with two fingers. Close syringe by attaching the luer-cap to the syringe cap.

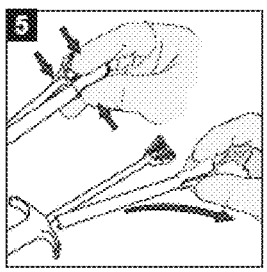

Step 5:
Remove the plunger sleeve from the mixing device by pushing the handle with the thumb and two fingers.

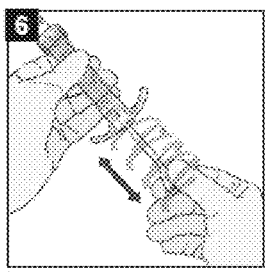

Step 6:
Mix the biomaterial by moving the mixing device back and forth while simultaneously rotating. Be sure to mix the material at both very ends of the syringe.

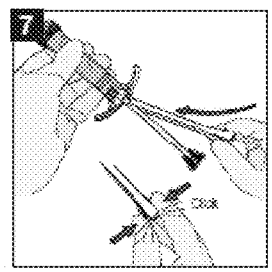

Step 7:
Pull back the mixing device completely. Attach the plunger sleeve onto the mixing device by positionning the front end to the piston first.

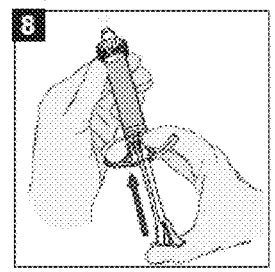

Step 8:
Remove the luer-cap from the syringe cap. To vent air slowly push the plunger until all air is removed.

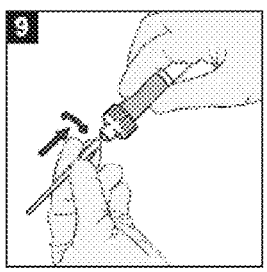

Step 9:
Attach accessory to the syringe.

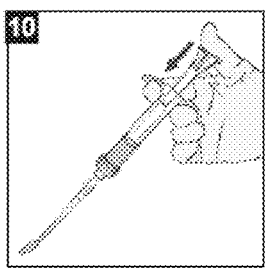

Step 10:
Push the plunger to dispense mixed biomaterial.

DRIED IMPLANT COMPOSITION AND INJECTABLE AQUEOUS IMPLANT FORMULATION

CROSS-REFERENCE TO RELATED APPLICATIONS

The present application claims priority benefit of European Patent Application No. 17207341.3, filed on Dec. 14, 2017, the disclosure of which is incorporated herein by reference.

BACKGROUND

The invention relates to a new dried implant composition for preparing a new injectable aqueous implant formulation for use in tissue regeneration, notably oral tissue regeneration, in particular in regeneration of alveolar bone, root cementum or the periodontal ligament (PDL), that is apt to be injected into periodontal pockets through a tapering system and a gauge 18 cannula, as well as the new injectable aqueous implant formulation prepared using that dried implant composition, a process and a kit for preparing that new injectable aqueous implant formulation.

There are a number of risk factors for periodontal disease such as poor oral hygiene, tobacco smoking, diabetes, obesity, genetic disposition, age and socio-economic status that facilitate bacterial accumulation, biofilm formation and infection of the gingival sulcus and hence the formation of a gingival inflammation or gingivitis. If left untreated, the inflammation progresses along the tooth root and causes destruction of the PDL and the surrounding alveolar bone, which is then referred to periodontitis. As periodontal disease progresses, pockets develop between tooth and the soft tissue and continue to grow until the tooth loses its stability and may fall off. Clinical signs of periodontal disease are inflammation of soft tissues, bleeding on (tissue-) probing, possibly accompanied with suppuration, and radiographic loss of alveolar bone. A dentist can determine the presence and extent of periodontal disease using a probe to measure the depth of periodontal pockets, i.e. the depth between soft tissue or bone and the tooth, which is referred to the loss of clinical (tooth) attachment.

Guided Tissue Regeneration (GTR) is a widely used surgical procedure to treat the loss of periodontal structures. In this procedure, the periodontist obtains access to the diseased root and surrounding bone by incisions of the soft tissues to raise a flap. The next step is debridement of the diseased bone, soft tissues and the root surface by suitable hand instruments, ultrasonic or laser devices where diseased tissues are removed and the root surface is scaled and planed. After debridement larger bone defects are filled with a bone regeneration material. Guided tissue regeneration barriers such as Geistlich Bio-Gide®, described in EP-B1-1676592 and commercially available from Geistlich Pharma AG, are placed over the bone regeneration material in deeper osseous defects. The periodontist closes the flap by appropriate sutures. Then, the gingiva, epithelial attachment, bone and periodontal attachment between the bone and tooth reform. While this procedure has been effective, incisions in the gingiva cause patient discomfort, pain, swelling, gingival recession, sensitive teeth, a long healing time and increase the possibility of re-infection.

Numerous natural and synthetic materials and compositions have been used as bone regeneration materials at the site of a bone defect.

A well-known natural, osteoconductive bone substitute material that promotes bone growth in periodontal osseous defects is Geistlich Bio-Oss®, commercially available from Geistlich Pharma AG. That material is manufactured from natural bone by a process described in U.S. Pat. Nos. 5,167,961 and 5,417,975, which enables preservation of the trabecular architecture and nanocrystalline structure of the natural bone, resulting in an excellent osteoconductive matrix which is not or very slowly resorbed.

To reduce the above-mentioned drawbacks related to incisions in the gingiva, there is a need for an injectable implant formulation.

For easy acceptance by patients when injected into periodontal pockets and convenient manual injection using a syringe, that injectable aqueous implant formulation should be extrudable through a cannula not larger in diameter than a gauge 18 (0.838 mm inner diameter) cannula or needle, preferably with a force not exceeding 60 N.

For optimal oral tissue regeneration, in particular for regeneration of alveolar bone, root cementum or the periodontal ligament, it is desirable that the injected implant formulation provides a matrix of hydroxyapatite and collagen close to the natural in vivo environment in which such regeneration takes place.

Hydroxyapatite derived from natural bone is closer to the natural in vivo environment in which regeneration takes place than synthetic (non-biological) hydroxyapatite or ceramic.

Particles that are obtained by grinding hydroxyapatite derived from natural bone have a more irregular and longitudinal shape than the rounded particles obtained by grinding synthetic hydroxyapatite or ceramic: They thus present a higher risk of clogging a gauge 18 cannula. See FIG. 5 which represents on the left-hand-side a scanning electron micrograph (SEM) of nanocrystalline hydroxyapatite particles derived from natural bone and on the right-hand-side a SEM of synthetic beta-TCP particles. Results of extrusion through cannulae of formulations containing synthetic hydroxyapatite or ceramic particles are thus only partly predictive of extrusion of similar formulations containing hydroxyapatite particles derived from natural bone.

One important feature of human natural bone is the morphology and the very small size (nano-size) of the hydroxyapatite crystals, which for human bone mineral is: hexagonal space group $P6_3/m$, about 30 to 50 nm in length (c axis: [0,0,1]) and 14 to 25 nm in length (a and b axes: [1,0,0] and [0,1,0]). See Weiner, S. et al., 1992, FASEB, 6:879-885. To be closer to the natural environment in which regeneration takes place it is thus desirable to use nanocrystalline hydroxyapatite particles derived from natural bone, preferably with a morphology and size of crystals close to those of human natural bone.

U.S. 2012/0107401 describes flowable implantable osteoconductive matrices that comprise a mixture of 0.1-2 mm mineral particles of either ceramic such as synthetic hydroxyapatite and beta-TCP or hydroxyapatite derived from natural bone, collagen that can be soluble collagen or insoluble collagen derived from a human or animal source, and a therapeutic agent including a statin. Those flowable implantable osteoconductive matrices are taught to be suitable as putties or as gels that can be injected, sprayed or instilled to the target tissue site. The w/w ratio of ceramic to collagen is taught to be 0.15 to 22.5 (claims 4) or 1.5 to 11.5 (claim 5), the only specific ratios of ceramic to collagen disclosed being 5 and 4.83 (claims 2 and [0089], [0090]).

U.S. Pat. No. 7,322,825 discloses a method of treating periodontal disease by injection into periodontal pockets of a composition which is a mixture of finely ground bone particles of microcrystalline hydroxyapatite having a size of 50 to 400 μm and "free collagen" particles of less than 1 mm in diameter, those "free collagen" particles being taught to be non-crosslinked collagen small fibrils or gel containing fibrillar collagen and optionally a physiologically compatible thickener. That mixture only has a low enough viscosity to pass through an 18 gauge (0.838 mm inner diameter) needle, after an additional energy infusion by application of heat, e.g. through microwave radiation. According to that patent, crosslinked collagen such as Avitene or Collastat cannot be cut in pieces small enough to go through an 18-gauge needle. For specifically described compositions, the w/w ratio of hydroxyapatite to collagen is 0.5 to 1.5.

The method of treating periodontal disease of U.S. Pat. No. 7,322,825 has not met wide-spread use. Non-crosslinked collagen such as "free collagen" is far from a natural in vivo environment that is desirable for oral tissue regeneration, in particular for regeneration of alveolar bone, root cementum or the periodontal ligament.

U.S. Pat. No. 5,352,715 discloses an injectable ceramic formulation for soft and hard tissue repair and augmentation which comprises collagen and calcium phosphate ceramic particles in a pharmaceutically acceptable fluid carrier, wherein the calcium phosphate ceramic particles have a size of 50 to 250 μm and the w/w ratio of the phosphate ceramic particles to collagen is from 1/19 to 1/1, preferably from 1/4 to 1/2. According the teaching of that patent, calcium phosphate ceramic particles are preferably sintered ceramic particles of non-biological (synthetic) origin and the collagen is substantially free from crosslinking, i.e. deprived of telopeptides, the preferred collagen being a purified atelopeptide reconstituted collagen. That injectable ceramic formulation can pass through a 20 gauge (0.603 mm inner diameter) needle.

A combination of telopeptide deprived collagen and synthetic calcium phosphate particles is far from the natural in vivo environment in which regeneration takes place.

EP-0270254-A2 discloses a dried implant composition comprising a mixture containing, by weight exclusive of moisture, 2-40% of reconstituted fibrillary atelopeptide collagen which is substantially free from crosslinking and 60-98% of a tricalcium phosphate such as hydroxyapatite with a size range 100-2000 μm, the mass ratio of tricalcium phosphate to atelopeptide collagen being thus from 1.5 to 49. That dried implant composition is treated with gamma radiation to improve both biological and handling properties.

A combination of collagen deprived of telopeptides and synthetic tricalcium phosphate particles is far from the natural in vivo environment in which regeneration takes place.

An injectable aqueous implant formulation containing collagen cannot be sterilized by gamma- or X-ray-irradiation. Stability over a long period (more than 6 months) of a sterile injectable aqueous implant composition would require drastic aseptic conditions of preparation and storage which are not always readily available: It is therefore desirable to provide a dried implant composition which is stable over a long period and apt to give by rehydration an injectable aqueous implant formulation.

SUMMARY OF THE INVENTION

The problem or objective of the invention is to find a dried implant composition that can be used to prepare an injectable aqueous implant formulation for use in oral tissue regeneration, in particular regeneration of alveolar bone, root cementum or the PDL, that injectable aqueous implant formulation being extrudable through a tapering system and a gauge 18 cannula and not having the drawbacks of the implant formulations of the prior art.

By varying the methods of preparation, the components and the proportions of components in more than 300 prototypes of dried implant compositions comprising hydroxyapatite particles derived from natural bone and naturally crosslinked fibrous collagen and submitting the formulations obtained by rehydration and homogeneous mixing of the dried implant compositions to an extrusion test using a gauge 18 cannula (described in Example 9), the inventors have found features of those dried implant compositions that unexpectedly provide extrudability through a tapering system and a gauge 18 cannula of the rehydrated and homogeneously mixed aqueous implant formulations, the latter providing a matrix close to the natural environment in which regeneration takes place.

That above objective is attained by the invention as defined in the appended claims.

The invention concerns:

a dried implant composition consisting essentially of a mixture of nanocrystalline hydroxyapatite particles derived from natural bone having a size of 50 to 200 μm and fragments of a naturally crosslinked fibrous collagen material that pass through a 0.5 mm sieve, whereby the w/w ratio of hydroxyapatite to collagen is from 1.8 to 4.5, the use of that dried implant composition for preparing by rehydrating and homogeneous mixing of 25-45 w/w % of the above dried implant composition with a pharmaceutically acceptable aqueous vehicle, an injectable aqueous implant formulation for use in oral tissue regeneration that is extrudable through a tapering system and a gauge 18 (0.838 mm inner diameter) 25.4 mm long cannula, and an injectable aqueous implant formulation for use in oral tissue regeneration which can be extruded through a tapering system and an 18 gauge (0.838 mm inner diameter) 25.4 mm long cannula with a force not exceeding 60 N, which comprises 25-45 w/w % of the above dried implant composition rehydrated and homogeneously mixed with sterile water or a sterile isotonic saline solution.

The term "consists essentially of a mixture of . . . " means that a very high proportion, usually at least 99% by weight of the dried implant consists of the recited mixture and at most 6% of a mineral salt, such as e.g. sodium chloride, the other components, usually at most 1% by weight of the dried implant, being derived from a natural source and not significantly affecting the extrusion behavior of the injectable aqueous implant formulation. Such components might be fat, sulfated ash, glucosamine, galactosamine and parts of residual proteins in very small quantities such as periostin, decorine and lumican or similar proteins. The other components do not include any synthetic polymer, in particular any polyethylene oxide, any polypropylene oxide, or any synthetic lubricant. The other components do not include any statin or any artificial hydroxyapatite, i.e. hydroxyapatite of non-biological origin.

The "nanocrystalline hydroxyapatite particles derived from natural bone" are particles derived from natural bone by a process enabling preservation of the nanocrystalline structure of the natural bone. Such a process must be performed at a temperature sufficiently low such that there is no recrystallization of the mineral part of natural bone, usually a temperature not exceeding 700° C.

A suitable such process is disclosed in U.S. Pat. No. 5,167,961 or 5,417,975: It involves degrading organic matter in degreased bone by heating with ammonia, extracting the solubilized degradation products by washing with flowing water at temperatures below 60° C. and treating the bone mineral in air at temperatures between 250° C. and 600° C., such as to enable preservation of the trabecular structure and nanocrystalline structure of natural bone, giving nanocrystalline hydroxyapatite with a very low organic impurity or protein content. The nanocrystalline hydroxyapatite particles derived from natural bone may be obtained by grinding and sieving the above nanocrystalline hydroxyapatite.

The nanocrystalline hydroxyapatite particles derived from natural bone may also conveniently be obtained by grinding and sieving Geistlich Bio-Oss® Small Granules (available from Geistlich Pharma AG, CH-6110, Switzerland).

The "nanocrystalline hydroxyapatite particles derived from natural bone" suitable for incorporation into the composition of the invention have a size of 50 to 200 µm.

Indeed, when the nanocrystalline hydroxyapatite particles derived from natural bone have a size over 200 µm, the implant formulation obtained by rehydration and homogeneous mixing tends to clog syringe cannulas of gauge 18 (0.838 mm inner diameter) and when the nanocrystalline hydroxyapatite particles derived from natural bone have a size below 50 µm, there is an increased risk of inflammation caused by those small particles.

The range size of 50 to 200 µm is thus critical.

Preferably those nanocrystalline hydroxyapatite particles derived from natural bone have a size of 100 to 180 µm. The risks of inflammation or clogging are then minimized.

The term "naturally crosslinked fibrous collagen material" means fibrous collagen material derived from a natural tissue material by a process allowing to retain its telopeptide structure and most of its natural crosslinking. Such naturally crosslinked fibrous collagen material is an insoluble collagen material that has not been submitted to any enzyme treatment, any chemical crosslinking or any physical crosslinking (such as e.g. by DeHydroThermal treatment DHT, UV irradiation etc. . . . ). Indeed, any of the latter treatments may significantly change the telopeptide structure and/or the natural crosslinking present in the natural tissue material.

The naturally crosslinked fibrous collagen material is suitably derived from tissues of natural origin which contain 50 to 100 w/w % collagen and 0 to 50 w/w % elastin, preferably 70 to 95 w/w % and 5 to 30% w/w elastin, as measured by desmosine/iodesmosine determination according to a modification of a known method involving hydrolysis and RP-HPLC (see e.g. Guida E. et al. 1990 *Development and validation of a high performance chromatography method for the determination of desmosines in tissues* in Journal of Chromatography or Rodriguqe P 2008 *Quantification of Mouse Lung Elastin During Prenatal Development* in The Open Respiratory Medicine Journal). Examples of such tissues include vertebrate, in particular mammalian (e.g. porcine, bovine, equine, ovine, caprine, lapine) peritoneum or pericardium membrane, placenta membrane, small intestine submucosa (SIS) and dermis. Such tissues are preferably porcine, bovine or equine. Interesting tissues are porcine, bovine or equine peritoneum membrane and dermis.

Preferably the naturally crosslinked fibrous collagen material is selected from the group consisting of porcine dermis and porcine peritoneum or pericardium membrane.

Usually the collagen is predominantly collagen type I, collagen type III or a mixture thereof. The collagen may also include a proportion of notably collagen type II, type IV, type VI or type VIII or any combination of those or any collagen types.

Usually the naturally crosslinked fibrous collagen material contains 50 to 100 w/w % collagen and 0 to 50 w/w % elastin, preferably 70 to 95 w/w % and 5 to 30% w/w elastin.

A suitable naturally crosslinked fibrous collagen material derived from a natural tissue is a collagen membrane from porcine, bovine or equine peritoneum or pericardium prepared by a process similar to that described in "Example" of EP-B1-1676592, comprising an alkaline treatment, an acid treatment and a treatment by organic solvents, followed by mincing into fragments that go through a 0.5 mm sieve.

Another suitable naturally crosslinked fibrous collagen material derived from a natural tissue is the Geistlich (commercially available from Geistlich Pharma AG) that has been minced into fragments that go through a 0.5 mm sieve.

Another suitable naturally crosslinked fibrous collagen material derived from a natural tissue is porcine dermis prepared by a process similar to that described in Example 7 of EP-B1-2654816, comprising an alkaline treatment, an acid treatment, freeze-drying and cleaning by organic solvents, followed by mincing into fragments that go through a 0.5 mm sieve.

It is interesting that the naturally crosslinked fibrous collagen material includes mature collagen fibres showing triple helicity as shown by Circular Dichroism Spectroscopy. Such fibres indeed form a scaffold that favours colonization by oral tissue regeneration cells, in particular cells for regeneration of bone and cells for regeneration of the PDL.

The naturally crosslinked fibrous collagen material must be present in fragments that pass through a 0.5 mm sieve. Such fragments are generally obtained by milling the naturally crosslinked fibrous collagen by a procedure involving a centrifugal mill and sieving of the collagen fragments.

The feature of the naturally crosslinked fibrous collagen material of being present in fragments that pass through a 0.5 mm sieve is critical for extrusion through a tapering system and a gauge 18 (0.838 mm inner diameter) cannula. Indeed, as shown by experiments performed on numerous prototypes, when larger fragments of the naturally crosslinked material, e.g. fragments that go through a 0.6 or 0.7 mm sieve are used in the dried implant composition, there is a substantial risk of the implant formulation obtained by rehydration and homogeneous mixing of the dried implant composition clogging the gauge 18 cannula.

The w/w ratio of hydroxyapatite to collagen is another critical parameter for extrusion through a tapering system and a gauge 18 (0.838 mm inner diameter) cannula.

Indeed, as shown by experiments performed on numerous prototypes, when the w/w ratio of hydroxyapatite to collagen is below 1.8 or above 4.5, the implant formulation obtained by rehydration and homogeneous mixing is not readily injectable, the force required for extrusion through a tapering system and a gauge 18 (0.838 mm inner diameter) cannula being too high. This is an unexpected result for which there seems to be no straightforward explanation. The force required for extrusion steeply increases from 1.8 to 4.5 but only moderately increases from 4.5 to 6. However, as shown by experiments performed on numerous prototypes, when the ratio is more than 4.5, e.g., 5, reproducibility of the force required for extruding the implant formulation is not sufficient. The high reproducibility required for a commercial implant product is attained only when the ratio of hydroxyapatite to collagen is from 1.8 to 4.5.

The range of the w/w ratio of hydroxyapatite to collagen from 1.8 to 4.5 is thus critical.

Preferably the w/w ratio of hydroxyapatite to collagen is from 2.5 to 4.2. Within that range the force required for extrusion is usually smaller.

Most preferably the w/w ratio of hydroxyapatite to collagen is from 2.5 to 4.0. The highest reproducibility of the extrusion results with a small force has indeed been found for injectable aqueous implant formulations with that w/w ratio of hydroxyapatite to collagen.

For enhancing extrudability of the injectable aqueous implant formulation it is suitable that the dried implant composition has been sterilized by gamma- or X-ray irradiation, using the usual radiation doses for sterilization, typically 27-33 kGy. Such a treatment indeed breaks certain bonds in the naturally crosslinked fibrous collagen and thus favours its flowability and extrudability.

The term "injectable aqueous implant formulation" refers to the implant formulation prepared by rehydration and homogeneous mixing of 25-45 w/w % of the dried implant composition with a pharmaceutically acceptable aqueous vehicle, which is capable of being conveniently injected into the human or animal body for oral tissue regeneration, in particular in periodontal pockets, being extrudable through a tapering system and gauge 18 (0.838 mm inner diameter) 25.4 mm long cannula.

Usually the injectable aqueous implant formulation is extrudable through a tapering system and gauge 18 (0.838 mm inner diameter) 25.4 mm long cannula with a force not exceeding 60 N.

Generally, that pharmaceutically acceptable aqueous vehicle is sterile water, a sterile isotonic saline solution, blood or fractions thereof, usually the patient's own blood.

The injectable aqueous implant formulation is preferably obtained by hydration and homogeneous mixing of 25-45 w/w % of the dried implant composition, more preferably 30-40 w/w % of the dried implant composition, with sterile water, a sterile isotonic saline solution or blood. When using that quantity of the dried implant composition, the injectable aqueous implant formulation is a new formulation that is extrudable from a syringe through a tapering system and an 18 gauge (0.838 mm inner diameter) 25.4 mm long cannula with a force not exceeding 60 N.

When the injectable aqueous implant formulation is obtained by hydration and homogeneous mixing of 30-40 w/w % of the above defined dried implant composition with sterile water or sterile isotonic saline solution, the force necessary to extrude the injectable aqueous implant formulation through a tapering system and an 18 gauge (0.838 mm inner diameter) 25.4 mm long cannula is below 40 N, preferably below 20 N.

When the injectable aqueous implant formulation is obtained by hydration and homogeneous mixing of 30-40 w/w % of the above defined dried implant composition with blood, the force necessary to extrude the injectable aqueous implant formulation containing 30-40 w/w % of the dried implant composition in a pharmaceutically acceptable vehicle is below 45 N, preferably below 25 N. The dried implant composition used in the invention may be prepared by a process comprising the following steps:

(a) Providing nanocrystalline hydroxyapatite particles derived from natural bone having a size of 50 to 200 μm,
(b) Preparing milled naturally crosslinked fibrous collagen material by a process comprising an alkaline treatment, an acid treatment and a treatment by organic solvents, and mincing into fragments that pass through a 0.5 mm sieve,
(c) Adding the milled naturally crosslinked fibrous collagen mixing obtained in (b) to an aqueous solution, vigorously mixing such as to obtain a collagen slurry, adding the hydroxyapatite particles having a size of 50 to 200 μm prepared in (a) and vigorously mixing, the pH remaining from 4.2 to 7.5,
(d) Drying the mixed composition containing hydroxyapatite particles and collagen obtained in (c) and
(e) Sterilizing by gamma- or X-ray irradiation the dried implant composition obtained in (d).

The nanocrystalline hydroxyapatite particles of ceramic derived from natural bone are particles derived from natural bone by a process enabling preservation of the nanocrystalline structure of the natural bone, as described above.

The high purity bone mineral obtained by the above process may be ground and sieved such as to have the required size.

Alternatively, particles of ceramic derived from natural bone having the required size may be produced from Geistlich Bio-Oss® (commercially available from Geistlich Pharma AG) using grinding and sieving steps.

The milled naturally crosslinked fibrous collagen of step (b) may be prepared by a process similar to that described in Example 7 of EP-B1-2654815, which comprises grinding in water porcine, bovine, equine, caprine or lapine hides to pieces of 0.5 to 30 mm, removing the water using a water soluble solvent such as an alcohol or ketone, defatting using a chlorinated hydrocarbon such as dichloroethane or methylene chloride or a non-chlorinated hydrocarbon such as hexane or toluene, treating the collagen with a strong inorganic base at a pH above 12.0 and with a strong inorganic acid at a pH of 0 to 1, freeze-drying and cleaning the dry collagen fibres of the sponge obtained by organic solvents such as alcohols, ethers, ketones and chlorinated hydrocarbons, removing the solvents under vacuum, and further mincing the cleaned collagen sponge into fragments that go through a 0.5 mm sieve by a procedure involving a centrifugal mill and sieving of the collagen fragments.

The milled naturally crosslinked fibrous collagen of step (b) may also be prepared by a process similar to that described in EP-B1-1676592, which comprises freeing from flesh and grease by a mechanical treatment porcine, bovine, equine, peritoneum or myocardium membranes, washing with water, treating with a 1-5% sodium hydroxide solution, washing with water, acidifying with 0.2-0.8% hydrochloric acid, washing with water until a pH 3.5, neutralizing with a $NaHCO_3$ solution, washing with water, dehydrating with a water soluble solvent such as an alcohol or ketone, degreasing with an hydrocarbon such as hexane, and further mincing the cleaned collagen membranes into fragments that go through a 0.5 mm sieve by a procedure involving a centrifugal mill and sieving of the collagen fragments.

In step (c) the milled naturally crosslinked fibrous collagen prepared in step (b) is added to an aqueous solution and vigorously mixed such as to obtain a collagen slurry, then hydroxyapatite particles having a size of 50 to 200 μm prepared in step (a) are added to and vigorously mixed with the collagen slurry.

Usually the pH measured in step (c) is from 4.2 to 7.5, preferably from 4.5 to 7.5.

Step (d) generally comprises drying the mixed composition containing hydroxyapatite particles and collagen obtained in (c) by freeze-drying or air drying preferably under reduced pressure.

The water content of the dried implant composition obtained in step (b) is generally 3-7% as measured by Karl Fischer titration.

Step (d) is optionally followed by step (e) of sterilization by gamma- or X-ray irradiation, generally using the usual radiation doses for sterilization, typically 27-33 kGy.

The invention further relates to a new injectable aqueous implant formulation for use in oral tissue regeneration which can be extruded through a tapering system and an 18 gauge (0.838 mm inner diameter) 25.4 mm long cannula with a force not exceeding 60 N, which comprises 25-45 w/w % of the dried implant composition of any of claims 1 to 6 rehydrated and homogeneously mixed with sterile water or a sterile isotonic saline solution.

When the injectable aqueous implant formulation comprises 30-40 w/w % of the dried implant composition rehydrated and homogeneously mixed with sterile water or a sterile isotonic saline solution, the force necessary to extrude the injectable aqueous implant formulation through a tapering system and an 18 gauge (0.838 mm inner diameter) 25.4 mm long cannula, is below 40 N, preferably below 20 N.

It has been observed that bone forming cells can grow in vitro in the injectable aqueous implant formulation of the invention. This shows the high biocompatibility of that injectable aqueous implant formulation which provides upon implantation a matrix very close to the natural in vivo environment in which regeneration takes place.

The invention also concerns a process for preparing the above injectable aqueous implant formulation which comprises rehydrating and homogeneously mixing 25-45 w/w %, respectively 30-40 w/w %, of the above defined dried implant composition with sterile water or sterile isotonic saline solution.

Homogeneous mixing of the rehydrated material is essential for its extrusion from the syringe with a low force.

It is convenient to perform rehydrating and homogeneously mixing of the dried implant composition with sterile water or a sterile isotonic saline solution in a syringe equipped with a mixing device.

An appropriate such syringe is Medmix syringe mixing system (MEDMIX, SP 003-00M-02/B, catalogue number 507211) represented in FIG. 1.

The invention further concerns a ready-to-use syringe containing the injectable implant formulation.

Such a ready-to-use syringe may be prepared long before injection under very strict sterile conditions by preparing the above defined dried implant formulation and rehydrating and homogeneously mixing 25-45 w/w % of the above defined dried implant composition with sterile water or a sterile isotonic saline solution and introducing into the syringe injectable aqueous implant formulation.

Such a ready-to-use syringe may also be prepared shortly before injection from a syringe equipped with a mixing device which contains the above dried implant composition by rehydrating and homogeneously mixing in the syringe that dried implant composition with sterile water, a sterile isotonic saline solution or blood.

The invention also relates to a kit for preparing the above injectable aqueous implant formulation for use in oral tissue regeneration, which comprises:
- a syringe equipped with a mixing device which contains a dried implant composition as defined above, a tapering system and a gauge 18 (0.838 mm inner diameter) 25.4 mm long cannula
- a container filled with an appropriate amount of sterile water or sterile isotonic solution.

Preferably the container filled with an appropriate amount of sterile water or sterile isotonic solution is a syringe with a cannula. The liquid can thus conveniently be introduced into the syringe equipped with a mixing device which contains the dried implant composition.

The invention further relates to a method of promoting regeneration of alveolar bone, root cementum or the PDL by implanting in the oral cavity the above injectable implant formulation.

BRIEF DESCRIPTION OF THE DRAWINGS

The invention will be described in further detail with reference to illustrative examples of preferred embodiments of the invention and the accompanying figures in which:

FIG. 2 is a copy of the Medmix mixing procedure as set out in the Operating Instruction which is attached to the Medmix syringe mixing system.

DETAILED DESCRIPTION

Figure 1:
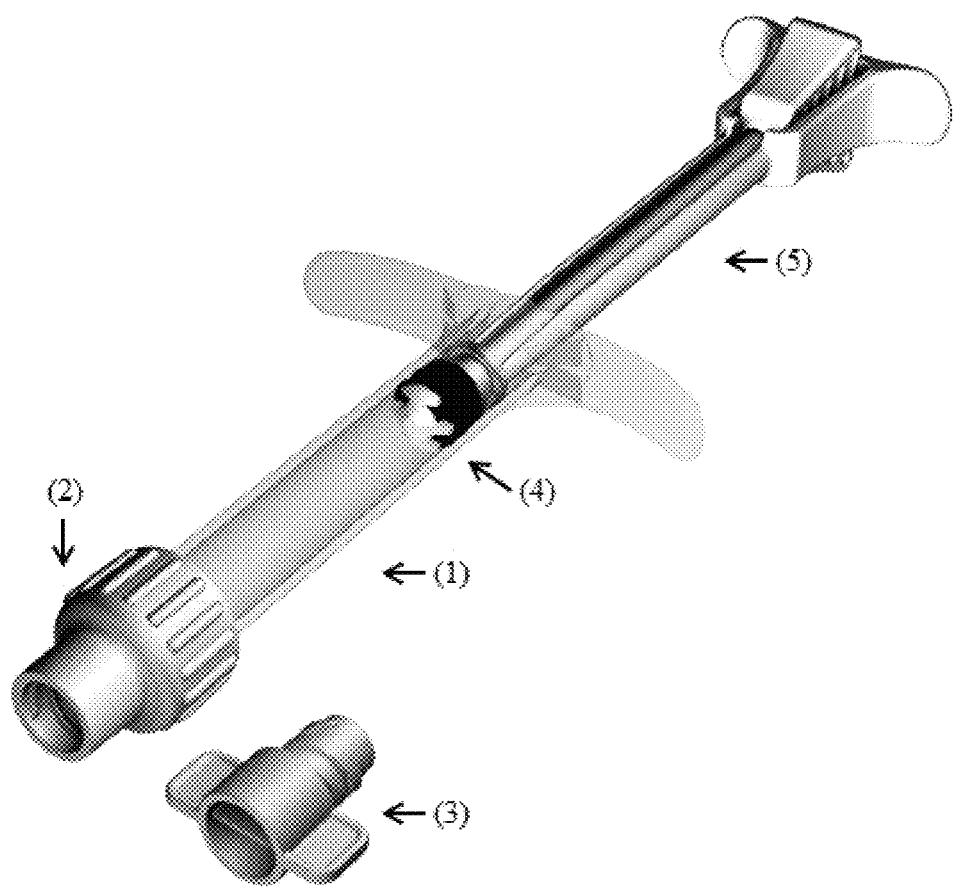
FIG. 1 represents the Medmix syringe mixing system (MEDMIX, SP 003-00M-02/B, catalogue number 507211), (1) being the syringe containing the dry biomaterial, (2) being the syringe cap with an open bore luer outlet, which is compatible with any luer cannula, (3) being the open bore cap to close the syringe during the mixing process, (4) being the mixing device, which is a flexible mixer once the plunger has been removed and (5) being the plunger, that can be removed to mix the material in the syringe and can be reset afterwards to push out the material.

The following examples illustrate the invention without limiting its scope.

Example 1 Preparation of the Raw Materials

1) Preparation of Hydroxyapatite Fine Particles Having a Size of 100 to 150 µm or 125 to 180 µm Hydroxyapatite bone mineral fine particles were produced from cortical or cancellous bone as described in Examples 1 to 4 of U.S. Pat. No. 5,417,975, using an additional sieving step between 100 and 150 µm or 125 to 180 µm, respectively.

Alternatively, hydroxyapatite bone mineral fine particles were produced by grinding Geistlich Bio-Oss® Small Granules (available from Geistlich Pharma AG, CH-6110, Switzerland), careful impaction using a piston and an additional sieving step between 100 and 150 µm or 125 to 180 µm, respectively.

The above prepared hydroxyapatite bone mineral fine particles having a size of between 100 and 150 µm or 125 to 180 µm were stored in glass bottles until use.

2) Preparation of Collagen A

Porcine hides were ground in a meat grinder to pieces of 1 to 20 mm. The water was removed using a water soluble solvent such as an alcohol or a ketone. The collagen fibres were defatted using a chlorinated hydrocarbon such as dichloroethane or methylene chloride or a non-chlorinated hydrocarbon such as hexane or toluene. After removing the solvent, the collagen was treated with a strong inorganic base at a pH above 12 for a period of 6 to 24 hours and treated with a strong inorganic acid at a pH of 0 to 1 for a period of 1 to 12 hours. The excess acid was removed by rinsing with water and the suspension was homogenized to a 0.5 to 2% homogenous suspension of collagen fibres in the presence of a swelling regulator such as an inorganic salt. The suspension was dried by freeze-drying and the dry collagen fibres of the sponge obtained was successively cleaned with different organic solvents such as alcohols, ethers, ketones and chlorinated hydrocarbons, the solvents being then evaporated under vacuum to a solvent residue of less than 1%.

1×1 cm pieces of the cleaned collagen sponge were cut by hand using scissors. The cut pieces were further minced by using first a cutting mill which includes a sieve of 0.5 to 4.0 mm, then a centrifugal mill (Retsch, ZM200) with a 0.5 mm sieve including trapezoid holes. The scissor cut pieces were alternatively milled directly with the centrifugal mill.

Collagen A consisting of naturally crosslinked fibrous collagen fragments that pass through a 0.5 mm sieve was thus obtained.

3) Preparation of Collagen B

The peritoneal membranes from young pigs were completely freed from flesh and grease by mechanical means, washed under running water and treated with 2% NaOH solution for 12 hours. The membranes were then washed under running water and acidified with 0.5% HCl. After the material had been acidified through its entire thickness (about 15 min) the material was washed until a pH of 3.5 was obtained. The material was then shrunk with 7% saline solution, neutralised with 1% $NaHCO_3$ solution and washed under running water. The material was then dehydrated with acetone and degreased with n-hexane.

The material was dried using ethanol ether and milled with a cutting mill (e.g. Pulverisette 25 from Fritsch: see www-.fritsch.de./produkte/mahlen/schneidmuehlen/pulverisette-25 or SM300 from Retsch: www.retsch.de/de/produkte/zerkleinern/schneidmuehlen.htlm) which includes a trapezoidal sieve of 0.5 to 1.0 mm.

The cut collagen fibre segments were further minced by using a centrifugal mill (Retsch, ZM200) with a 0.5 mm sieve including trapezoid holes.

Collagen B consisting of naturally crosslinked fibrous collagen fragments that pass through a 0.5 mm sieve was thus obtained.

Example 2 Drying and Sterilization of Mixed Compositions Containing Hydroxyapatite Particles and Collagen The mixed compositions containing hydroxyapatite particles and collagen (obtained as described in Examples 3 to 8 below) were dried by freeze-drying or air drying under reduced pressure and sterilized by gamma-ray or X-ray irradiation.

1) Freeze-Drying

From the 50 ml syringe the mass was filled up in 1 ml Cyclic Olefin Copolymer (COC) syringes from back side. Approximately 0.5 ml volume was filled up per 1 ml syringe. The syringes were stored closed from both sides for 5 hours in a fridge at 4° C. Then the syringes were opened on both sides and put on a metal plate in the lyophilisator, each syringe being in a lying down position such as have a large surface of contact with the metal plate. Then the following lyophilisation program was initiated:
1. Freezing in 7 hours to −40° C.
2. Holding 4 hours at −40° C.
3. Primary drying at −10° C. and 850 µbar during 20 hours
4. Secondary drying at +20° C. and 100 µbar during 6 hours Alternatively, the viscous collagen-hydroxyapatite mass was not freeze-dried in syringes, but on stainless steel plates or in small stainless steel forms of less than 25 mm in diameter and less than 10 mm in depth. The dry obtained material after freeze drying was crushed into particles of 0.1 to 2 mm in size by using a centrifugal mill (Retsch, ZM200) with 1.5 mm up to 10 mm sieves. Crushing by a mill led to smaller hydroxyapatite particles in the reconstituted end product.

Alternatively, for crushing the viscous collagen-hydroxyapatite mass was extruded out of a standard luer outlet of a syringe and formed as straight lines on stainless steel plates. Then the material was freeze dried as such.

2) Air Drying

The viscous collagen-hydroxyapatite mass e.g. formed as straight lines was alternatively dried by air in a vacuum oven at 30° C. and 10 mbar for 24 hours.

The dried straight lines were broken into 5 to 10 mm long sticks by hand.

The granulated material or the small sticks was then filled in a 3 ml syringe mixing system (MEDMIX, SP 003-00M-02/B, catalogue number 507211) with syringe cap with open bore luer and open bore cap (MEDMIX, CP 000-76M/D, catalogue number 506964).

3) Sterilization

The dried implant composition obtained by lyophilisation or air drying under reduced pressure was sterilized in the syringe by gamma-ray or X-ray irradiation with 27-33 kGy. The water content in the dried product just after sterilisation was 3-7%, as measured by Karl Fisher titration.

Example 3 Preparation of Dried Implant Composition 1 Containing Hydroxyapatite Particles Having a Size of 100 to 150 µm or 125 to 180 µm and Collagen A, with a w/w Ratio of Hydroxyapatite to Collagen of 4.0

Preparation of the Collagen-Hydroxyapatite Composition

Water and hydrochloric acid (2M) were mixed in a beaker with a spatula. The milled collagen A obtained in Example 1 was added and carefully pushed into the liquid to wet all the collagen. The beaker was closed with a screw lid and the water-collagen slurry was homogenously mixed by Speedmixer (CosSearch GmbH, Speedmixer DAC400.1FVZ) during 4 minutes with 2500 rpm. The collagen slurry was slightly heated up during the mixing procedure. Then the collagen slurry was cooled for 30 minutes in the fridge at 4° C.

The collagen slurry was mixed again by Speedmixer during 2 minutes with 2500 rpm. Then the hydroxyapatite bone mineral fine particles having a size of between 100 and 150 µm or 125 and 180 µm prepared in Example 1 were added in the beaker with the collagen slurry and the mass was mixed by Speedmixer during 2 minutes with 2000 rpm. The resulting pH was around 4.5.

The material quantities used in the experiments above are specified in the following table:

| Material | Net weight [g] |
| --- | --- |
| Water | 6.36 |
| HCl 2 mol/l | 0.64 |
| Collagen A | 0.60 |
| Hydroxyapatite particules 100-150 µm or 125-180 µm | 2.40 |

Drying of the Hydroxyapatite-Collagen Composition

Drying by freeze-drying or air drying under reduced pressure and sterilization was performed as described in Example 2.

Dried implant composition 1 containing hydroxyapatite particles having a size of 100 to 150 µm or 125 to 180 µm and collagen A with a w/w ratio of hydroxyapatite to collagen of 4.0 and giving a pH of 4.5 after rehydration with demineralised water performed as described in Example 9, was thus obtained.

Example 4 Preparation of Dried Implant Composition 2 Containing Hydroxyapatite Particles Having a Size of 125 to 180 µm and Collagen B, with a w/w Ratio of Hydroxyapatite to Collagen of 4.0

Preparation of the Collagen-Hydroxyapatite Composition

The milled collagen B obtained in Example 1 was carefully pushed into demineralized water to wet all the collagen. The beaker was closed with a screw lid and the water-collagen slurry was homogenously mixed by Speedmixer during 1 minute with 2500 rpm. The collagen slurry was then heated up to 70° C. in a water bath during 4 hours. Then the collagen slurry was cooled for 30 minutes at ambient temperature or in a fridge or in a water bath.

The collagen slurry was mixed again by Speedmixer during 2 minutes with 2500 rpm. Then the hydroxyapatite bone mineral fine particles having a size of between 125 and 180 µm prepared in Example 1 were added in the beaker with the collagen slurry and the mass was mixed by Speedmixer during 2 minutes with 2000 rpm. The resulting pH was 6.2.

The material quantities used in the experiments above are specified in the following table:

| Material | Net weight [g] |
| --- | --- |
| Water | 6.36 |
| Collagen B | 0.60 |
| Hydroxyapatite particules 125-180 µm | 2.40 |

Drying of the Hydroxyapatite-Collagen Composition

Drying by freeze-drying or air drying under reduced pressure and sterilization was performed as described in Example 2.

Dried implant composition 2 containing hydroxyapatite particles having a size of 125 to 180 µm and collagen B with a w/w ratio of hydroxyapatite to collagen of 4.0 and giving a pH of 6.2 after rehydration with demineralised water performed as described in Example 9, was thus obtained.

Example 5 Preparation of Dried Implant Composition 3 Containing Hydroxyapatite Particles Having a Size of 125 to 180 µm and a Mixture of 2 Parts of Collagen a for 1 Part of Collagen B, with a (w/w) Ratio of Hydroxyapatite to Collagen of 2.67

Preparation of the Collagen-Hydroxyapatite Composition

Water and hydrochloric acid (2M) were mixed in a beaker with a spatula. The milled Collagen B obtained in Example 1 was carefully pushed into the liquid to wet all the collagen. The beaker was closed with a screw lid and the water-collagen slurry was homogenously mixed by Speedmixer during 2 minutes with 2500 rpm with a resulting pH between 0.9 and 1. The collagen slurry was then heated up to 70° C. in a water bath during 20 minutes. Then the collagen slurry was cooled down for 30 minutes in a water bath at 25° C. The milled collagen A obtained in Example 1 was added and carefully pushed into the collagen slurry to wet all the collagen. Then the slurry was mixed by Speedmixer during 4 minutes with 2500 rpm.

Finally, the hydroxyapatite bone mineral fine particles having a size of between 125 and 180 µm prepared in Example 1 were added in the beaker with the collagen slurry and the mass was mixed by Speedmixer during 2 minutes with 2000 rpm. The resulting pH was around 4.5.

The material quantities used in the experiments above are specified in the following table:

| Material | Net weight [g] |
| --- | --- |
| Water | 6.08 |
| HCl 2 mol/l | 0.62 |
| Collagen A | 0.60 |
| Collagen B | 0.30 |
| Hydroxyapatite particules 125-180 µm | 2.40 |

Drying of the Hydroxyapatite-Collagen Composition

Drying by freeze-drying or air drying under reduced pressure and sterilization was performed as described in Example 2.

Dried implant composition 3 containing hydroxyapatite particles having a size of 125 to 180 µm and a mixture of 2 parts of collagen A for 1 part of collagen B, with a (w/w) ratio of hydroxyapatite to collagen of 2.67, and giving a pH of 4.5 after rehydration with demineralised water performed as described in Example 9, was thus obtained.

Example 6 Preparation of Dried Implant Composition 4 Containing Hydroxyapatite Particles Having a Size of 125 to 180 µm and a Mixture of 2 Parts of Collagen a for 1 Part of Collagen B, with a w/w Ratio of Hydroxyapatite to Collagen of 2.67

Preparation of the Collagen-Hydroxyapatite Composition

The milled Collagen B obtained in Example 1 was carefully pushed into demineralized water to wet all the collagen. The beaker was closed with a screw lid and the water-collagen slurry was homogenously mixed by Speedmixer during 1 minute with 2500 rpm. The collagen slurry was then heated up to 70° C. in a water bath during 20 min. Then the collagen slurry was cooled down for 30 minutes in a water bath at 25° C.

The milled collagen A obtained in Example 1 was added and carefully pushed into the collagen slurry to wet all the collagen. Then the slurry was mixed by Speedmixer during 4 minutes with 2500 rpm.

Finally, the hydroxyapatite bone mineral fine particles having a size of between 125 and 180 μm prepared in Example 1 were added in the beaker with the collagen slurry and the mass was mixed by Speedmixer during 2 minutes with 2000 rpm. The resulting pH was 6.0.

The material quantities used in the experiments above are specified in the following table:

| Material | Net weight [g] |
| --- | --- |
| Water | 6.70 |
| Collagen A | 0.60 |
| Collagen B | 0.30 |
| Hydroxyapatite particles 125-180 μm | 2.40 |

Drying of the Hydroxyapatite-Collagen Composition
Drying by freeze-drying or air drying under reduced pressure and sterilization was performed as described in Example 2.
Dried implant composition 4 containing hydroxyapatite particles having a size of 125 to 180 μm and a mixture of 2 parts of collagen A for 1 part of collagen B, with a w/w ratio of hydroxyapatite to collagen of 2.67, and giving a pH of 6.0 after rehydration with demineralised water performed as described in Example 9, was thus obtained.

Example 7 Preparation of Dried Implant Composition 5 Containing Hydroxyapatite Particles Having a Size of 125 to 180 μm and Collagen a, with a w/w Ratio of Hydroxyapatite to Collagen of 4.0

Preparation of the Collagen-Hydroxyapatite Composition
The milled Collagen A was carefully pushed into demineralized water to wet all the collagen. The hydroxyapatite bone mineral fine particles having a size of between 125 and 180 μm prepared in Example 1 were added and the beaker was closed with a screw lid. The water-collagen-hydroxyapatite slurry was homogenously mixed by Vortex mixer during 1 minute and a scoop during 1 minute.
The resulting pH was 6.1.
The used material quantities are described in the following table:

| Material | Net weight [g] |
| --- | --- |
| Water | 7.0 |
| Collagen A | 0.60 |
| Hydroxyapatite particles 125-180 μm | 2.40 |

Drying of the Hydroxyapatite-Collagen Composition
Drying by freeze-drying or air drying under reduced pressure and sterilization was performed as described in Example 2.
Dried implant composition 5 containing hydroxyapatite particles having a size of 125 to 180 μm and collagen A, with a w/w ratio of hydroxyapatite to collagen of 4.0, and giving a pH of 6.1 after rehydration with demineralized water performed as described in Example 9, was thus obtained.

Example 8 Preparation of Dried Implant Composition 6 Containing Hydroxyapatite Particles Having a Size of 125 to 180 μm and Collagen A, with a (w/w) Ratio of Hydroxyapatite to Collagen A of 2.0

Preparation of the Collagen-Hydroxyapatite Composition
The milled Collagen A was carefully pushed into demineralized water to wet all the collagen. The hydroxyapatite bone mineral fine particles having a size of between 125 and 180 μm prepared in Example 1 were added and the beaker was closed with a screw lid. The water-collagen-hydroxyapatite slurry was homogenously mixed by Vortex mixer during 1 minute and a scoop during 1 minute.
The resulting pH was 5.8.
The used material quantities are described in the following table:

| Material | Net weight [g] |
| --- | --- |
| Water | 7.0 |
| Collagen A | 1.0 |
| Bio-Oss 125-180 μm | 2.0 |

Drying of the Hydroxyapatite-Collagen Composition
Drying by freeze-drying or air drying under reduced pressure and sterilization was performed as described in Example 2.
Dried implant composition 6 containing hydroxyapatite particles having a size of 125 to 180 μm and collagen A, with a (w/w) ratio of hydroxyapatite to collagen of 2.0, and giving a pH of 5.8 after rehydration with demineralised water performed as described in Example 9, was thus obtained.

Example 9 Preparation of a Ready-to-Use Syringe Containing an Injectable Aqueous Implant Formulation by Rehydration of the Dried Implant Composition in the Syringe 1) Preparation of a ready to use syringe containing an injectable aqueous implant formulation obtained by rehydration and homogeneous mixing of the dried implant composition
   a) Using a 3-way stopcock valve Luer-Lok adapter and a 1 ml syringe
2) Dried, sterile hydroxyapatite-collagen compositions in the 1 ml product syringe were rehydrated by using a 3-way stopcock valve Luer (Luer-Lok) adapter (BD Connecta, 3-way stopcock, catalog number 394600), Vaclok syringes (Qosina, Vaclok syringe, catalog number C1097) and a normal single use supplementary syringe 1 ml (Luer-Lok).
   The liquid to rehydrate the collagen was demineralised water, an isotonic saline solution, a PBS solution of pH 7.4 containing 150 mM sodium phosphate buffer (prepared by dissolving $NaH_2PO_4$ in demineralised water and adjusting the pH with sodium hydroxide), or blood.
   The weight of the dry biomaterial (dried implant composition obtained in one of Examples 3 to 8) in the syringe was known or was measured. An amount of rehydrating liquid was filled in the supplementary syringe such as to obtain an injectable paste containing by weight 38% dry biomaterial.
   The product syringe was then connected to the 3-way stopcock valve and the 180° counterpart of the 3-way stopcock valve was closed by a closing cap. At the third position (90° from the product syringe) of the 3-way stopcock valve a 60 ml Vaclok Syringe was connected to the system. Air was evacuated from the product syringe by pulling the plunger of the Vaclok Syringe and locking at 50 ml volume. Then the 3-way valve was rotated by 180° to keep the vacuum in the product syringe, whereas the Vaclok Syringe was replaced by the supplementary syringe filled with liquid. Then the 3-way valve was rotated by 180°. Due to the vacuum, the liquid automatically flowed into the product syringe and wetted the product. To ensure the complete liquid transfer into the product syringe the plunger of the product syringe was drawn back. The material was rested for 30 seconds to enable hydration before the material was pushed from the product syringe into the supplementary syringe and back, this sequence repeated 40 times to obtain a homogeneously mixed material. After the mixing procedure the 3-way stopcock valve was replaced by the applicator which is a tapering system and a blunt end 18 gauge (inner diameter 0.838 mm) 25.4 mm long cannula.

The reconstituted injectable aqueous implant formulation obtained by rehydration and homogeneous mixing of each of the dried implant compositions 1 to 6 with demineralised water had a pH near to the pH measured before lyophilisation, namely about 4.5, 6.2, 4.5, 6.0, 6.1 and 5.8, respectively.

b) Using a 3 ml Medmix syringe mixing system

Alternatively the particles of the dried material were rehydrated with demineralised water, an isotonic saline solution, a PBS solution of pH 7.4 containing 150 mM sodium phosphate buffer or blood, in the Medmix syringe mixing system (MEDMIX, SP 003-00M-02/B, catalog number 507211) with syringe cap with open bore luer and open bore cap (MEDMIX, CP 000-76M/D, catalog number 506964), represented in FIG. 1 in which (1) is the syringe containing the dry biomaterial, (2) is the syringe cap with an open bore luer outlet, which is compatible with any luer cannula, (3) is the open bore cap to close the syringe during the mixing process, (4) is the mixing device, which is a flexible mixer once the plunger is removed, (5) is the plunger, that can be removed to mix the material in the syringe and can be reset afterwards to push out the material.

The Medmix mixing procedure set out in FIG. 2 was followed. To get an optimal result, after step 4 the plunger is pushed 3 times in order to push the liquid into the material to wet it and perform the mixing step (step 6) for 60 seconds. All the air is removed in step 8.

3) Extrusion test

The extrudability of the reconstituted injectable aqueous implant formulation obtained was tested with a tension and pressure testing device (Zwick & Roell, BT1-FR2.5TS.D14). The ready to use syringe prepared above was placed vertically in a syringe holding and the plunger was pressed down from the machine while the force of pressing the product out of the syringe through the applicator comprising a tapering system and a blunt end 18 gauge (inner diameter 0.838 mm) 25.4 mm long cannula (Nordson EFD, Precision Tip 18GA 1", catalog number 7018110), was measured with the following program:

Force till resistance: 0.1 N
Speed till resistance: 100 mm/min
Testing speed: 1 mm/s, position controlled
End of testing: force limit, 150 N
Force sensor: 200 N For all tested injectable implant formulations obtained by rehydration and homogeneous mixing with demineralised water, an isotonic saline solution or a PBS solution, notably for injectable implant formulations, which were prepared from dried implant compositions 1 to 6, the measured force did not exceed 40 N.

For all tested injectable implant formulations obtained by rehydration and homogeneous mixing with blood, notably for injectable implant formulations, which were prepared from dried implant compositions 1 to 6, the measured force did not exceed 45 N.

For injectable implant formulations obtained by rehydration and homogeneous mixing with demineralised water, an isotonic saline solution or a PBS solution, which were prepared from dried implant compositions 1, 2, 3, 5 and 6 the measured force did not exceed 20 N.

For injectable implant formulations obtained by rehydration and homogeneous mixing with blood, which were prepared from dried implant composition 1 (containing hydroxyapatite particles having a size of 100 to 150 µm or 125 to 180 µm and collagen A, with a w/w ratio of hydroxyapatite to collagen of 4.0) and dried implant composition 2 (containing hydroxyapatite particles having a size of 125 to 180 µm and collagen B, with a w/w ratio of hydroxyapatite to collagen of 4.0), the measured force did not exceed 25 N.

Figure 3A:
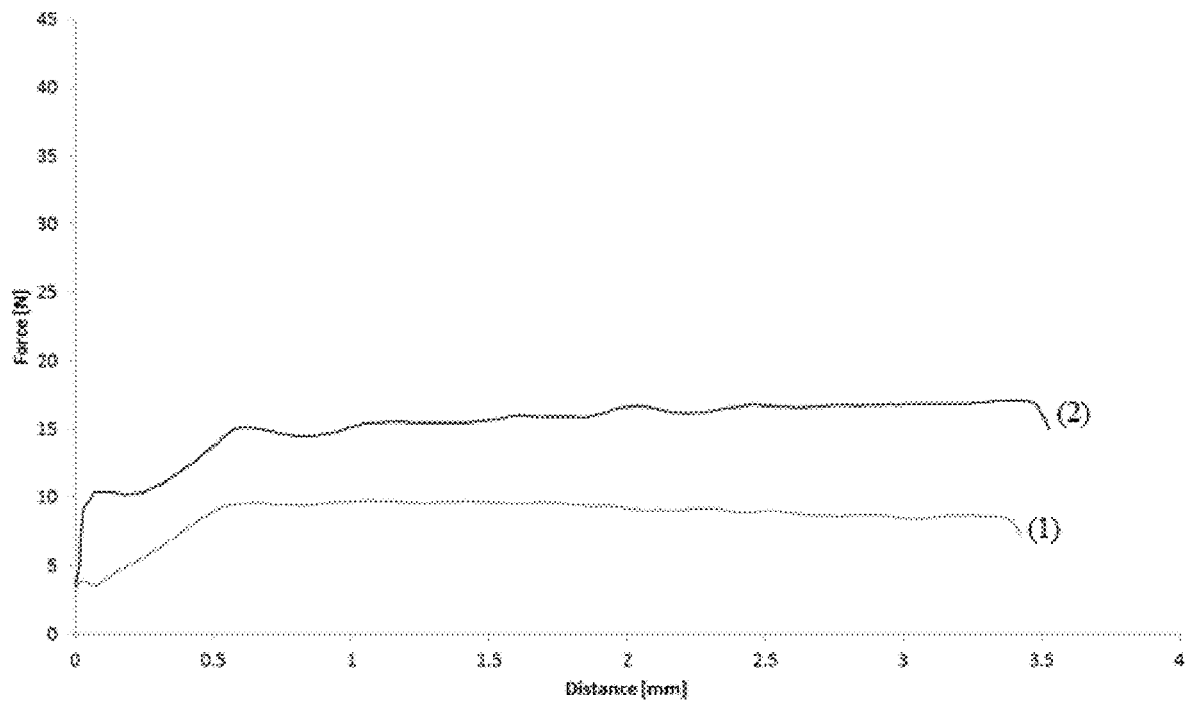
FIGS. 3A and 3B represent the extrusion curves of the injectable aqueous implant formulations obtained by rehydrating and homogeneously mixing dried implant compositions 2 and 4 in the examples with isotonic saline (curves (1) and (3)) or fresh human blood (curves (2) and (4)), respectively.
Figure 3B:
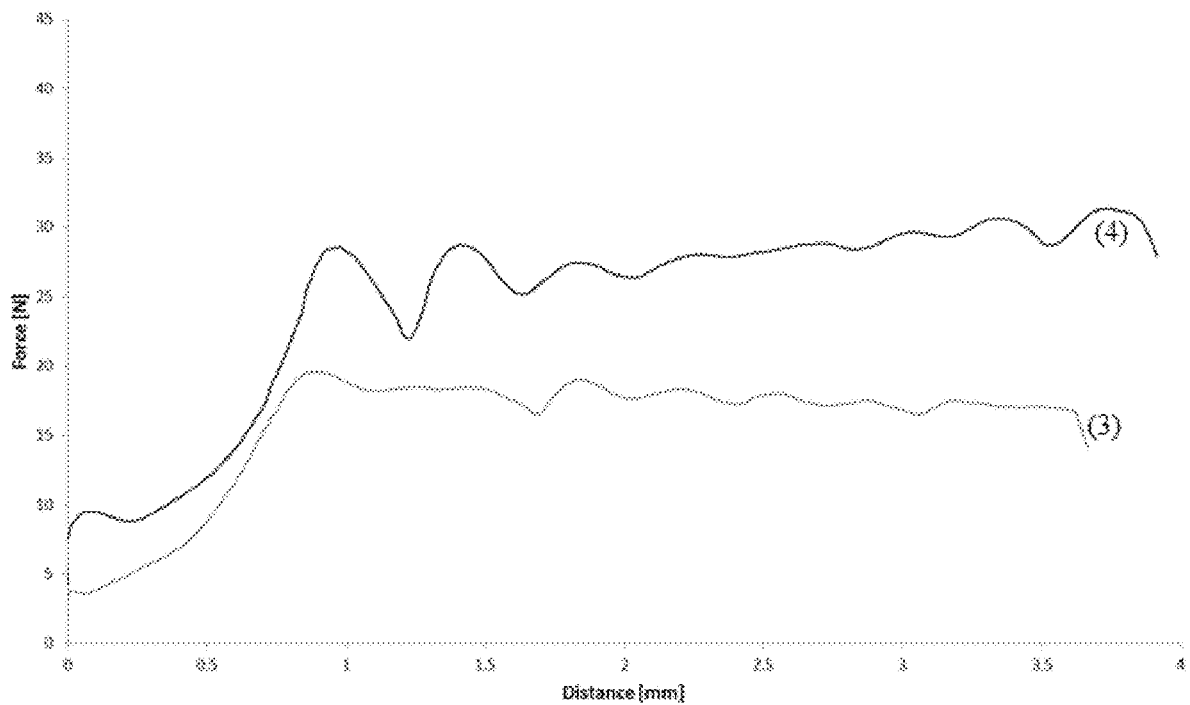

See FIGS. 3A and 3B, which represent the extrusion curves of the injectable implant formulations obtained by rehydrating and homogeneously mixing dried implant compositions 2 and 4 with isotonic saline or fresh human blood, respectively.

In FIG. 3A, (1) and (2) are the extrusion curves of dried implant composition 2 (containing hydroxyapatite particles having a size of 125 to 180 µm and collagen B, with a w/w ratio of hydroxyapatite to collagen of 4.0) rehydrated with isotonic saline and fresh human blood, respectively.

In FIG. 3B, (3) and (4) are the extrusion curves of dried implant composition 4 (containing hydroxyapatite particles having a size of 125 to 180 µm and a mixture of 2 parts of collagen A for 1 part of collagen B, with a w/w ratio of hydroxyapatite to collagen of 2.67) rehydrated with isotonic saline and fresh human blood, respectively.

Example 10 Biocompatibility: In Vitro Test on Growth of Two Bone Forming Cell Lines in the Injectable Aqueous Implant Formulation of the Invention The cells from:
MC3T3 CytoLight Red, a prosteoblast cell line originating from mouse calvaria (ATCC CRL-2593) that was transduced to express red fluorescent protein in the cytoplasm using Cytolight Red Lentivirus (Essen Bioscience), or MG63 (cell line derived from human osteosarcoma) were tested for their ability to colonize the injectable aqueous implant formulation of the invention as follows.

Those cells were cultivated under conditions recommended by the supplier, namely for MC3T3 Cytolight Red cells: culture in αMEM (GIBCO) supplemented with 10% fetal bovine serum (FBS, Lubio), 1% Penicillin-Streptomycin (GIBCO) and 0.5 µg/ml Puromycin (Sigma) and for MG63 cells: culture in DMEM (GIBCO) supplemented with 10%

Figure 4:
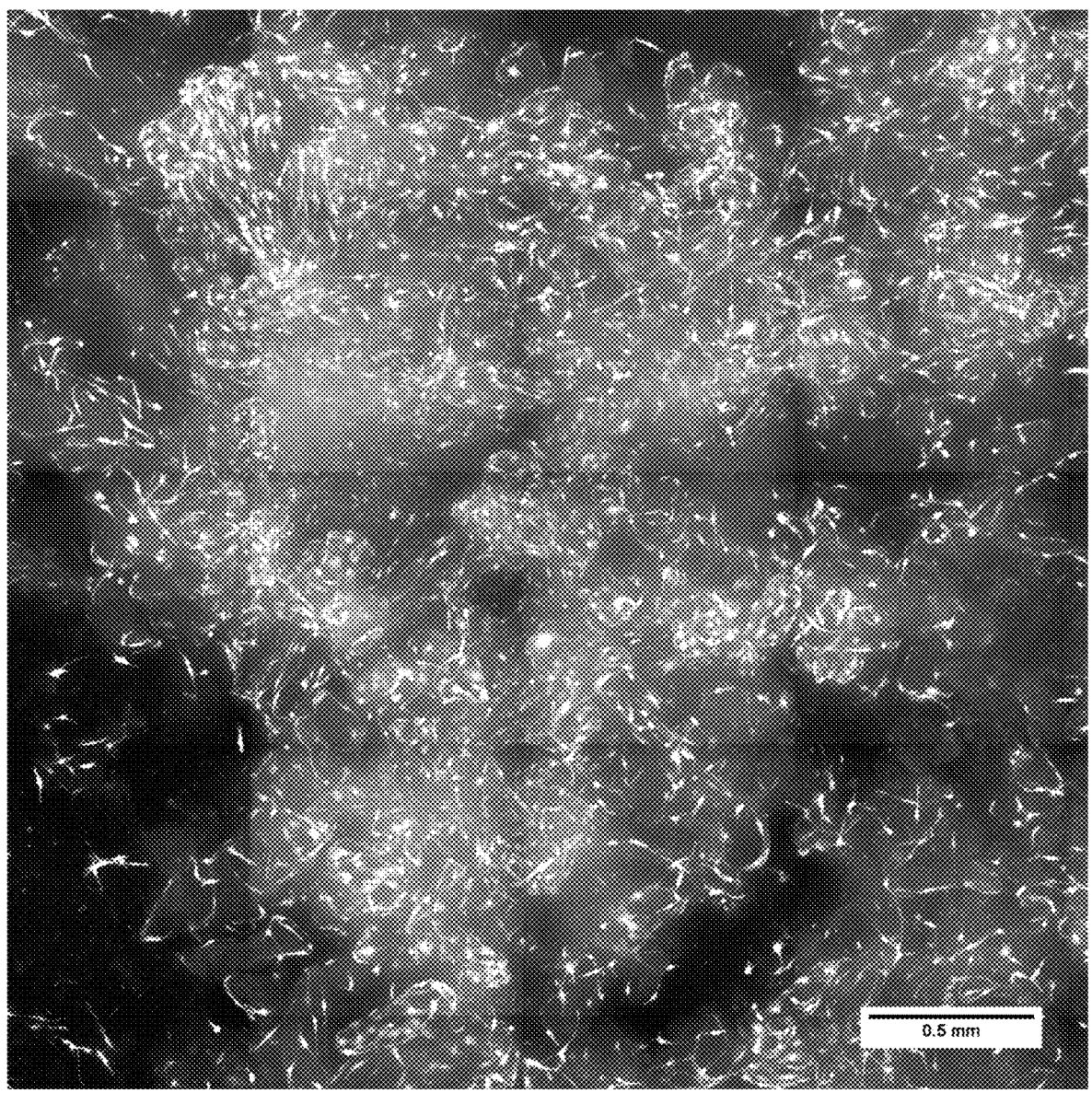
FIG. 4 is a microscopy image using a CV1000 confocal spinning disk microscope with excitation by 561 nm laser illumination of injectable aqueous implant formulation 4 obtained by rehydrating and homogeneously mixing dried implant composition 4 (prepared in Example 6) with human blood: the grown MC3T3 CytoLight Red cells are visualised in bright.
Figure 5:
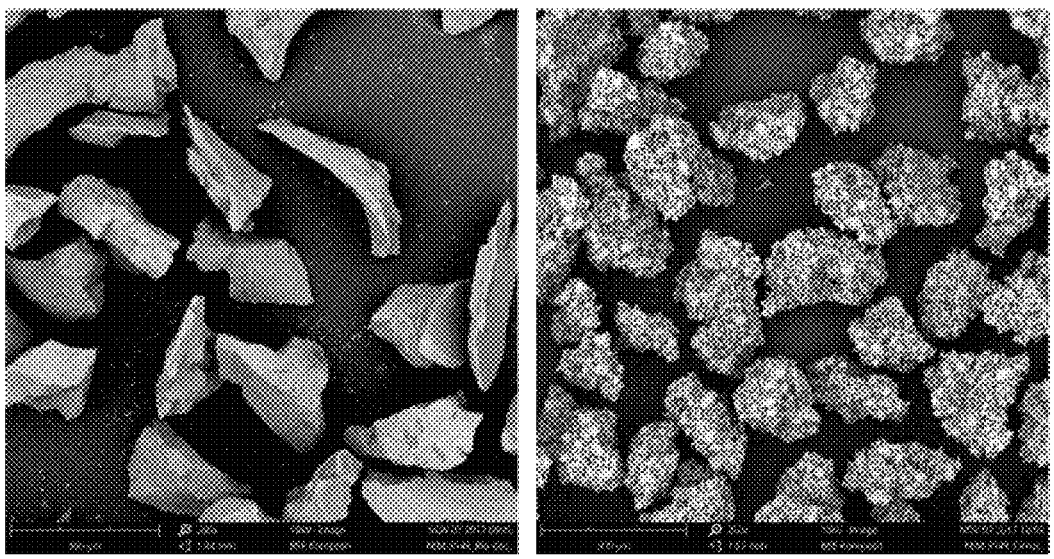
FIG. 5 represents on the left-hand-side a scanning electron micrograph (SEM) of nanocrystalline hydroxyapatite particles derived from natural bone and on the right-hand-side a SEM of synthetic beta-TCP particles.

FBS (Lubio), 1% Penicillin-Streptomycin (GIBCO). A layer of those cells was introduced into wells of a multiwall plate and about 1 ml of biomaterial was added on top of the layer of cells in each well using 3 ml Medmix syringes containing injectable implant formulations 1 to 4 obtained by rehydrating and homogeneously mixing dried implant compositions 1 to 4 (prepared in examples 3 to 6) with human blood or an isotonic saline solution. The cells were cultivated for 8 days. Those experiments showed for each of injectable implant formulations 1 to 4 colonization of the biomaterial by each the MC3T3 CytoLight Red and M63 cell lines. See FIG. 4, which is a microscopy image using CV1000 confocal spinning disk microscope (Yokogawa) with excitation by 561 nm laser illumination of injectable aqueous implant formulation 4 obtained by rehydrating and homogeneously mixing dried implant composition 4 (prepared in Example 6) with human blood: the grown MC3T3 CytoLight Red cells are visualised in bright.

Those experiments show that bone forming cells can grow in vitro in the injectable aqueous implant formulation of the invention. This demonstrates the high biocompatibility of that injectable aqueous implant formulation which provides upon implantation a matrix very close to the natural in vivo environment in which regeneration takes place.

The invention claimed is:

1. A dried implant composition consisting essentially of a mixture of nanocrystalline hydroxyapatite particles derived from natural bone having a size of 50 to 200 μm and fragments of naturally crosslinked fibrous collagen material that pass through a 0.5 mm sieve, whereby the w/w ratio of hydroxyapatite to collagen is from 1.8 to 4.5.

2. An injectable aqueous implant formulation for use in oral tissue regeneration, wherein the injectable aqueous implant formulation comprises 25-45 w/w % of a dried implant composition consisting essentially of a mixture of nanocrystalline hydroxyapatite particles derived from natural bone having a size of 50 to 200 μm and fragments of naturally crosslinked fibrous collagen material that pass through a 0.5 mm sieve, whereby the w/w ratio of hydroxyapatite to collagen is from 1.8 to 4.5, homogenized in a pharmaceutically acceptable aqueous vehicle wherein the injectable aqueous implant formulation having properties such that it is extrudable through a tapering system and an 18 gauge (0.838 mm inner diameter) 25.4 mm long cannula with a force not exceeding 60 N.

3. The injectable aqueous implant formulation of claim 2, wherein the formulation comprises 30-40 w/w % of the dried implant and having properties such that it is extrudable through a tapering system and an 18 gauge (0.838 mm inner diameter) 25.4 mm long cannula with a force not exceeding 40 N.

4. The injectable aqueous implant formulation of claim 2, wherein the dried implant composition has a w/w ratio of hydroxyapatite to collagen of from 2.5 to 4.2.

5. A ready to use syringe containing the injectable aqueous implant formulation of claim 2.

6. A kit for preparing the injectable aqueous implant formulation for use in oral tissue regeneration of claim 2 comprising:
   a) a syringe equipped with a mixing device and containing: a dried implant composition consisting essentially of a mixture of nanocrystalline hydroxyapatite particles derived from natural bone having a size of 50 to 200 μm and fragments of naturally crosslinked fibrous collagen material that pass through a 0.5 mm sieve, whereby the w/w ratio of hydroxyapatite to collagen is from 1.8 to 4.5; a tapering system; and a gauge 18 (0.838 mm inner diameter) cannula; and
   b) a container filled with an appropriate amount of sterile water or a sterile isotonic solution.

7. The kit of claim 6, wherein the container comprising sterile water or a sterile isotonic solution is a syringe with a cannula.

8. A process for preparing the injectable aqueous implant formulation of claim 2 comprising: providing a dried implant composition consisting essentially of a mixture of nanocrystalline hydroxyapatite particles derived from natural bone having a size of 50 to 200 μm and fragments of naturally crosslinked fibrous collagen material that pass through a 0.5 mm sieve, whereby the w/w ratio of hydroxyapatite to collagen is from 1.8 to 4.5; rehydrating and homogeneously mixing 25-45 w/w % of the dried implant composition in sterile water or a sterile isotonic saline solution.

9. The process of claim 8, comprising rehydrating and homogeneously mixing 25-45 w/w % the dried implant composition in a syringe equipped with a mixing device.

10. The process of claim 8 wherein providing the dried implant composition comprises the following steps:
    (a) preparing nanocrystalline hydroxyapatite particles having a size of 50 to 200 μm;
    (b) preparing milled naturally crosslinked fibrous collagen material by a process comprising an alkaline treatment, an acid treatment and a treatment by organic solvents, and mincing the naturally crosslinked fibrous collagen material into fragments that pass through a 0.5 mm sieve to obtain the milled naturally crosslinked fibrous collagen material;
    (c) adding the milled naturally crosslinked fibrous collagen mixing obtained in (b) to an aqueous solution, vigorously mixing the aqueous solution such as to obtain a collagen slurry, adding the nanocrystalline hydroxyapatite particles having a size of 50 to 200 μm prepared in (a) to the collagen slurry, whereby the w/w ratio of hydroxyapatite to collagen is from 1.8 to 4.5 , and vigorously mixing, at a pH from 4.2 to 7.5 to obtain a mixed composition,
    (d) drying the mixed composition containing hydroxyapatite particles and collagen obtained in (c) to obtain a dried implant composition; and
    (e) sterilizing by gamma- or X-ray irradiation the dried implant composition obtained in (d).

11. A method of treating a subject with an injectable aqueous implant formulation, wherein the subject is in need of oral tissue regeneration, comprising implanting the injectable aqueous implant formulation of claim 2 in an oral cavity of the subject by extruding the injectable aqueous implant formulation of claim 2 through a tapering system and a gauge 18 cannula (having an inner diameter of 0.838 mm) positioned in the implantation site.

12. The method of claim 11, further comprising, before said implanting:
    a) providing a dried implant composition that consists essentially of a mixture of nanocrystalline hydroxyapatite particles derived from natural bone having a size of 50 to 200 μm and fragments of naturally crosslinked fibrous collagen material that pass through a 0.5 mm sieve, whereby the w/w ratio of hydroxyapatite to collagen is from 1.8 to 4.5; and
    b) rehydrating 25-45 w/w % of the dried implant composition in a pharmaceutically acceptable aqueous vehicle and mixing to form the injectable rehydrated aqueous implant formulation.

13. The method of claim 12, wherein the dried implant composition has a w/w ratio of hydroxyapatite to collagen of from 2.5 to 4.2.

14. The method of claim 2, wherein in the dried implant composition the hydroxyapatite particles have a size from 100 to 180 µm.

15. The method of claim 12, wherein the dried implant composition has been sterilized by gamma- or X-ray irradiation.

16. The method of claim 12, wherein in the dried implant composition the naturally crosslinked fibrous collagen material is selected from the group consisting of porcine dermis and porcine peritoneum or pericardium membrane.

17. The method of claim 12, wherein the pharmaceutically acceptable aqueous vehicle is sterile water, a sterile isotonic saline solution, blood or fractions thereof.

18. The method of claim 11, wherein the subject is in need of regeneration of alveolar bone, root cementum or periodontal ligament and said implanting promotes regeneration of alveolar bone, root cementum or periodontal ligament in the subject's oral cavity.

19. The method of claim 18, wherein the injectable aqueous implant formulation is implanted into a periodontal pocket.

20. The method of claim 18, wherein the injected aqueous implant formulation provides a matrix of hydroxyapatite and collagen in the subject's oral cavity.

\* \* \* \* \*